United States Patent [19]

Pierce

[11] Patent Number: 4,825,866
[45] Date of Patent: May 2, 1989

[54] WOUND CLOSURE DEVICE

[76] Inventor: Robert Pierce, P.O. Box 307, Pittsburg, N.H. 03592

[21] Appl. No.: 90,768

[22] Filed: Aug. 27, 1987

[51] Int. Cl.$^4$ .............................................. A61B 17/04
[52] U.S. Cl. .................................................... 128/335
[58] Field of Search .................................. 128/335, 155

[56] References Cited

U.S. PATENT DOCUMENTS

| | | | |
|---|---|---|---|
| 3,528,426 | 9/1970 | Vukojevic | 128/155 |
| 3,667,462 | 6/1972 | Moon | 128/169 |
| 3,698,395 | 10/1972 | Hasson | 128/335 |
| 3,926,193 | 12/1975 | Hasson | 128/335 |
| 4,114,624 | 9/1978 | Haverstock | 128/335 |
| 4,210,148 | 7/1980 | Stivala | 128/335 |

Primary Examiner—Richard C. Pinkham
Assistant Examiner—Gary Jackson
Attorney, Agent, or Firm—John M. Brandt

[57] ABSTRACT

A closure device for skin wounds consisting of two semi-rigid base sheets each backed in part with a quantity of skin compatible self-adhesive. The sheets are placed on either side of a wound and have VELCRO (trademark) attaching means on their upper surfaces for drawing together and securing the opposite sides of the wound. A deformable resilient tube may be included on each sheet to provide a vertical force to either side of the wound as well.

2 Claims, 1 Drawing Sheet

WOUND CLOSURE DEVICE

BACKGROUND OF THE INVENTION

1. Field of the Invention

The invention resides in the field of medical bandages and more particularly relates to wound closure devices.

2. Description of the Prior Art

A number of bandage type devices for the sutureless closing of wounds exist in the prior art. The object of these inventions is to close and secure a wound without the use of sutures requiring additional needle punctures in the vicinity of the wound and the attendant possibility of secondary infections, and additional discomfort to the patient.

Examples of such prior art devices known to the inventor include U.S. Pats. No. 3,528,426, Vukojevic, showing a self-adhesive elastic closure bandage; U.S. Pat. No. 3,667,462, Moon, illustrating an orthopedic bandage secured by VELCRO; and U.S. Pat. No. 3,698,395, Hanson, disclosing a combination surgical drape and incision closure bandage.

As understood by the inventor all of the prior art devices employ a flexible based bandage in contrast to his semi-rigid base and none of these disclose a deformable resilient tube laterally disposed across each base to provide vertical pressure to either side of the wound.

SUMMARY OF THE INVENTION

The invention may be summarized as a wound closure device consisting of two separate semi-rigid base sheets which are attached to either side of the wound by skin compatible self-adhesive applied to at least a portion of each sheet. Each base sheet has a quantity of VELCRO (hook and loop) fastening material attached to the upper surface thereof. One sheet has VELCRO material extending beyond one edge so that the wound will be spanned when the device is in place. The other sheet has a quantity of the commensurate mating material.

When the sheets are in place and the VELCRO extension is tautly fastened to the opposite sheet, horizontal closure pressure is applied to the wound.

Additionally a resilient deformable tube may be placed laterally across the upper surface of the innermost (closest to the wound) edge of each sheet to transmit a vertical pressure to either side of the wound when the VELCRO extension is fastened as before. The tubing will further serve to form a bridge for the VELCRO extension across the wound such that the likelihood of any contact between the extension and the wound would be reduced and to further prevent bondage between the wound's drainage and bandage material. The tubes will further act as a bumper to limit further damage from accidental contact with foreign objects.

Thus the combination of the two features of semi-rigid sheet and resilient tube provide both horizontal and vertical pressure to a wound without the use of traditional absorbant bandage material. The wound can be left completely exposed for inspection or can be dressed with appropriate healing materials as desired. Unlike all other bandages, these two components consisting of non-porous non-absorbant material, will not affect the healing process by tearing the scab when removing the bandage.

The invention may be provided in a variety of sizes and edge shapes or may be cut to conform to a particular wound profile as required. As such, it is easily applied by a layman and is ideal for use in remote areas where professional medical assistance may not be available or for use at accident sites or in emergency rooms as a short term or intermediate bleeding control measure.

These and other features and advantages of the invention will be more clearly understood from the description of the preferred embodiment and drawings which follows.

DESCRIPTION OF THE PREFERRED EMBODIMENT

Figure 1:
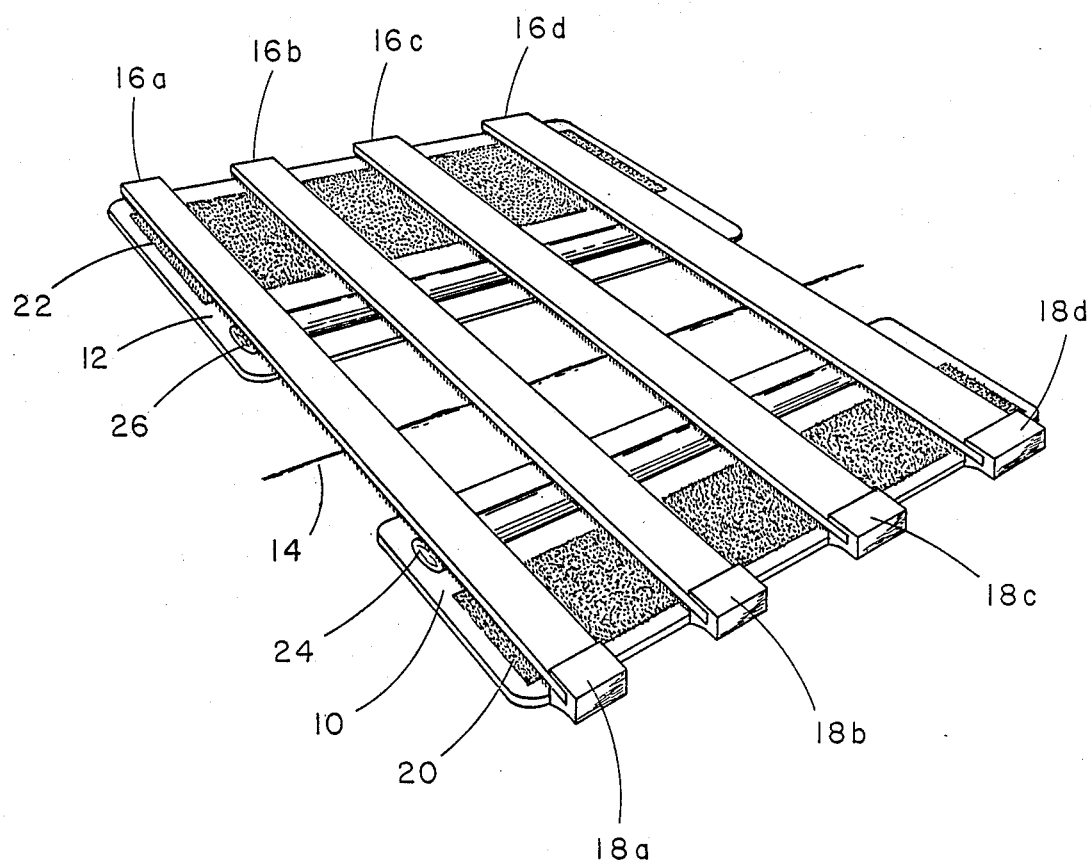
FIG. 1 is a perspective view of the preferred embodiment of the invention.

Referring to FIG. 1, a perspective view of the preferred embodiment of the invention is shown in which first semi-rigid base sheet 10 and second semi-rigid base sheet 12 are attached to either side of skin wound 14 by skin compatible self-adhesive. VELCRO fingers 16a, b, c, and d are attached to sheet 10 by, for example, integrally molded retaining fixtures 18a, b, c, and d. Base sheet 10 has a strip of mating VELCRO 20 disposed laterally on the upper surface and base sheet 12 has a similar strip 22.

Figure 2:
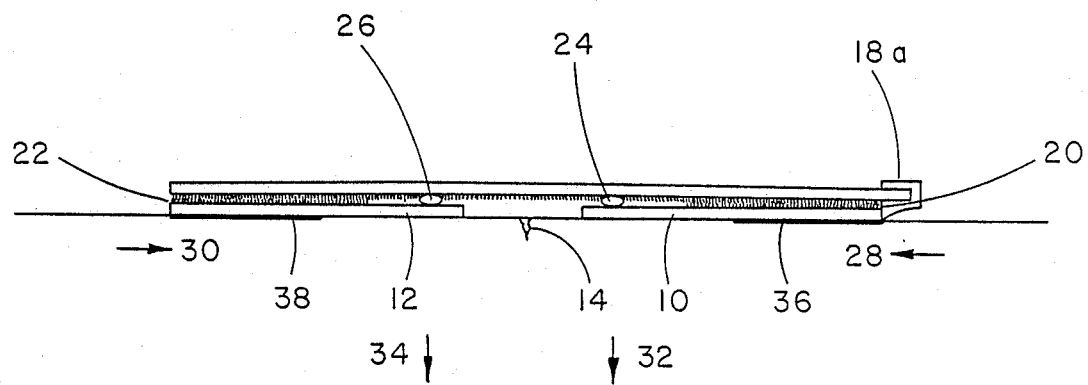
FIG. 2 is an elevation side view of the embodiment of FIG. 1.

Deformable resilient tubes 24 and 26 are laterally disposed on the upper surfaces of sheets 10 and 12 respectively. As indicated in FIG. 2 where like numerals denote like parts, tautly securing the fingers between sheets 10 and 12 draws the opposite sides of the wound together as indicated by arrows 28 and 30, and effects closure. Similarly tubes 24 and 26 transmit a downward or vertical pressure upon securing the fingers as indicated by arrows 32 and 34.

Further indicated in FIG. 2 is a partial layer of self-adhesive 36 and 38 attached to sheets 10 and 12 respectively. The purpose and function of the semi-rigid base sheets as opposed to the completely flexible materials of prior art devices will now be seen to be three-fold. First, such a material, plastic for example, will allow self-adhesive to be placed on only a portion of end base as the bases will not easily buckle or fold upon the application of horizontal force. Second, such a material will provide a support for the deformable resilient tubes for transmitting vertical pressure to further augment the closure of the wound. Third, the self-adhesive material can be substantially remote from the wound thereby eliminating possible contamination by the adhesive.

Variations of the preferred embodiment will become evident in view of the disclosure above. The invention is therefore defined by the following claims.

What is claimed is:

1. A closure device for skin wounds comprising in combination:

a. a first base sheet of non-porous non-absorbing semi-rigid material;

b. a second base sheet of non-porous non-absorbing semi-rigid material;

c. a quantity of skin compatible self-adhesive disposed on at least a portion of each of said first and second sheets whereby one each of said sheets may be placed and secured on either side of said wound;

d. a first flexible sheet of hook or loop material secured at one edge to said first base sheet, said flexible sheet of sufficient length to extend beyond the edge of said first base sheet to span said wound;

e. a second flexible sheet of mating hook or loop material secured in face to face relationship with said second base sheet in a position to receive and hold said first flexible sheet whereby the opposite sides of said wound will be horizontally drawn and secured together upon the application of said closure device; and f. a deformable resilient tube attached laterally to the upper surface at the innermost edge of each of said base sheets whereby a vertical force will be applied to the opposite sides of said wound upon the application of said closure device.

2. The apparatus of claim 1 wherein said first flexible sheet is divided into a plurality of spaced-apart fingers.

* * * * *